United States Patent [19]
McKay

[11] Patent Number: 5,824,554
[45] Date of Patent: Oct. 20, 1998

[54] DETECTION OF ALLERGENIC SUBSTANCES IN FOOD PRODUCTS

[76] Inventor: Florine M. McKay, 1403 Burr Ridge Club, Burr Ridge, Ill. 60521

[21] Appl. No.: 592,011

[22] Filed: Jan. 26, 1996

Related U.S. Application Data

[62] Division of Ser. No. 303,640, Sep. 9, 1994, abandoned.

[51] Int. Cl.[6] .................................................. G01N 33/02
[52] U.S. Cl. ............................... 436/20; 436/21; 436/22; 436/23; 436/24; 436/169; 422/55; 422/56; 422/57; 422/58; 422/61; 426/231; 426/232; 116/201; 116/206
[58] Field of Search .................................. 436/20, 21, 22, 436/23, 24, 169; 422/55, 56, 57, 58, 61; 426/231, 232; 116/201, 206

[56] References Cited

U.S. PATENT DOCUMENTS

| | | | |
|---|---|---|---|
| 2,129,754 | 9/1938 | Yagoda | 422/56 |
| 2,249,867 | 7/1941 | Snelling | 435/805 |
| 2,626,855 | 1/1953 | Hand | 422/56 |
| 2,998,353 | 7/1961 | Ryan | 435/805 |
| 2,999,052 | 9/1961 | Albaum | 435/805 |
| 3,006,735 | 10/1961 | Jordan | 23/230 |
| 3,010,880 | 11/1961 | Littman et al. | 435/805 |
| 3,139,328 | 6/1964 | Jacob | 23/253 |
| 3,245,882 | 4/1966 | Guthrie | 435/805 |
| 3,615,226 | 10/1971 | Apter | 23/230 R |
| 3,785,930 | 1/1974 | Ellis | 435/805 |
| 3,819,490 | 6/1974 | Klingstrom et al. | 435/805 |
| 3,915,639 | 10/1975 | Friedenberg | 23/230 |
| 4,056,359 | 11/1977 | Janin | 23/259 |
| 4,308,028 | 12/1981 | Elkins | 23/230 |
| 4,349,353 | 9/1982 | Blumenthal et al. | 23/230 R |
| 4,518,565 | 5/1985 | Boger et al. | 422/58 |
| 4,677,059 | 6/1987 | Beutler et al. | 435/25 |
| 4,918,391 | 4/1990 | Byrd | 324/446 |
| 4,962,025 | 10/1990 | Moldowan | 435/25 |
| 5,071,623 | 12/1991 | Akutsu | 422/56 |
| 5,306,466 | 4/1994 | Goldsmith | 422/58 |
| 5,388,043 | 2/1995 | Hettinger | 364/413.29 |

*Primary Examiner*—Timothy McMahon
*Assistant Examiner*—Sharidan Carrillo
*Attorney, Agent, or Firm*—Andrus, Sceales, Starke & Sawall

[57] ABSTRACT

A method and device for the detection of allergenic substances in food products. The device comprises a dining mat, such as a doily, formed of an absorbent material and small spots of reagents are applied to isolated zones on the mat. Each reagent is characterized by the ability to change its characteristics when contacted by an allergenic substance. A label can be applied to the mat adjacent each reagent indicating the respective allergenic substance. In use, a small amount of a food product is applied to a reagent and if the food product contains the allergenic substance, the reagent will change its appearance indicating the presence of the allergenic substance in the food product.

2 Claims, 1 Drawing Sheet

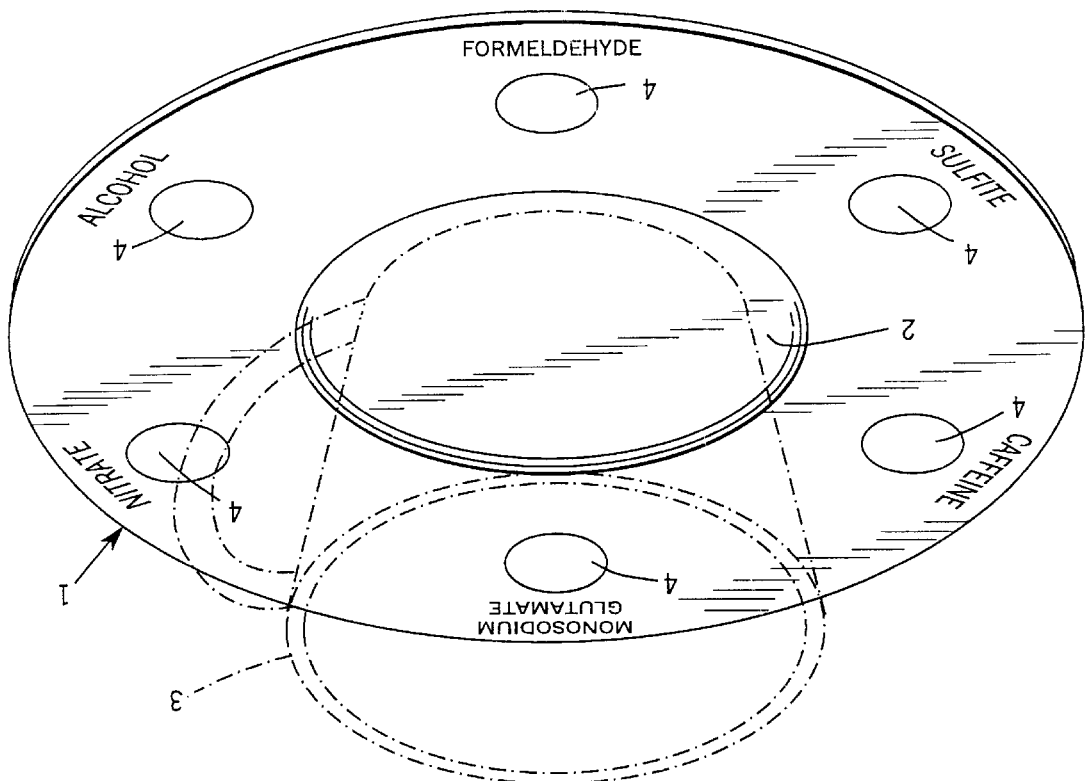

DETECTION OF ALLERGENIC SUBSTANCES IN FOOD PRODUCTS

This is a divisional application of Ser. No. 08/303,640 filed Sept. 9, 1994, now abandoned.

BACKGROUND OF THE INVENTION

In the past, various types of dipsticks have been used to indicate the presence of certain substances or conditions in liquid materials. For example, U.S. Pat. No. 3,006,735 employs a dipstick to determine the hardness of water. In that patent, the dipstick is impregnated at spaced areas with color responsive substances, each of which changes color at a particular hardness level.

In U.S. Pat. No. 3,139,328 a paper dipstick is employed to determine the pH of a liquid. In this construction, various areas of the paper are impregnated with solutions of different indicators, each adapted to undergo a color change in a different part of the pH range.

U.S. Pat. No. 4,308,028 shows a device for the microscopic examination of a liquid specimen such as urine, utilizing a strip having a plurality of reagent pads that provide a chemical test for materials such as protein, glucose, blood and the like.

A drug abuse dipstick is disclosed in U.S. Pat. No. 3,915,639 in which drug abuse compounds are detected by the use of an ion exchange dipstick in combination with a stain producing reagent which will react with the various drug abuse compounds to form colored products.

A large number of people are allergic to substances that may be present in food products, such as, for example, caffeine, alcohol, formaldehyde, monosodium glutamate and the like. If the food is prepared at home a consumer is normally aware of the contents of the food product so that the consumer can avoid the use of the allergenic substance. However, when eating out in a restaurant, or other dining establishment, the consumer is not aware of the presence of an allergenic substance in the food product, and consumption of the food product may cause a violent allergic reaction. Even inquiring from the food server or the chef as to whether the product contains the allergenic substance may not be sufficient, as in some cases neither the food server nor the chef may be fully aware of the contents of the food product.

Therefore, there has been a need for a simple and convenient manner for the detection of allergenic substances in food products.

SUMMARY OF THE INVENTION

The invention is directed to a device and method for the detection of allergenic substances in food products, such as those that may be found in restaurants, fast food establishments, and other eating establishments.

In accordance with the invention, the device consists of a dining mat, such as a doily or placemat, that is preferably composed of an absorbent material, such as paper. Small dabs or spots of reagents are applied to isolated zones on the mat, and each reagent is characterized by the ability to change its characteristics, such as color, when contacted by an allergenic substance. Each reagent is reactive to a different allergenic substance, such as, for example, caffeine, formaldehyde, monosodium glutamate, sulfites, alcohol, and the like. Labels can be applied to the mat adjacent each reagent indicating the allergenic substance associated with that reagent.

In use, a small amount of a food product is applied to a reagent spot through use of a swab, a food utensil such as a spoon, or through use of a tubular device such as a straw. If the food product contains the allergenic substance, the reagent will change its characteristic, such as its color, to indicate the presence of the allergenic substance in the food product.

The invention provides a simple and convenient manner of detecting allergenic substances in food products. The mat or doily can be conveniently carried by the diner or consumer and can be used during dining as a doily for a coffee cup, glass or the like.

The food product can be applied to the reagent by any desired method such as, for example, a cotton tip swab, spoon, drinking straw or the like.

As the invention requires that the food product be applied to the mat, there is no possible contamination of the food product as could occur if the reagents were applied to a dipstick which was immersed in the food product.

Other objects and advantages will appear during the course of the following description.

DESCRIPTION OF THE DRAWING

The drawing illustrate the best mode presently contemplated of carrying out the invention.

The drawing is a perspective view of the device for the detection of allergenic substances in food products.

DESCRIPTION OF THE ILLUSTRATED EMBODIMENT

The drawing illustrates a dining mat 1 in the form of a doily which can be employed for the detection of allergenic substances. It is contemplated that the dining mat may also take the form of a placemat. Mat 1 is preferably formed of an absorbent material, such as paper.

Mat 1 includes a central area 2 and when used as a doily the central area 2 serves to receive a coffee cup or container 3.

In accordance with the invention, small dabs or spots of reagents 4 are applied to the upper surface of mat 1. Each reagent is reactive to a specific allergenic substance and is characterized by the ability to change its characteristics, such as color, when contacted by that allergenic substance. Each reagent 4 differs from the other reagents on the mat.

As shown in the drawing, the reagent spots 4 are preferably spaced from the outer periphery of the mat, and are located in circumferentially spaced relation about the center area 2.

Examples of allergenic substances that can be detected are caffeine, alcohol, formaldehyde, monosodium glutamate, sulfites, nitrates, and the like.

The reagents are materials that are reactive with the specific allergenic substances to produce a change in appearance or color. For example, the reagent for formaldehyde, as described in *Spot Test Analysis*, by Ervin Jungreis, Wiley & Sons, 1985, is xylene, and the reaction between formaldehyde and xylene leads to the formation of Bis-(dimethyl)-diphenyl methane which provides a pink color.

The presence of ethanol can be detected using permanganate as the reagent as disclosed in *Spot Tests in Organic Analysis* by Fritz Feigl, Elsevier Publishing Company, 1966.

The reagent to be used for detecting nitrates can be phenoldisulfonic acid as described in *Colorimetric Methods of Analysis* by Snell, D. Van Nostrand Co., Inc. 1959, while the presence of sulfates can be determined by using potassium dichromate as a reagent also as described in *Colorimetric Methods of Analysis*, supra.

When detecting the presence of caffeine, Mayer's, Wagner's and Dragendorff's reagents can be employed as described in the *Forensic Application of Spot Test Analysis*.

As shown in the drawing, suitable labels can be applied adjacent each reagent or spot zone 4 indicating the specific allergenic substance to which the reagent applies. In addition, instructions as to use of the device can also be applied to the upper surface of mat 1, preferably in the central area 2. Such instructions could read as follows:

"Apply food product to appropriate spot to detect presence of allergenic substance"

In use, a small amount of the food product is applied to the spot or zone 4 to determine whether the foods product contains that specific allergenic substance. If the food product is a solid material, the product can be applied to the spot 4 using a spoon or other eating instrument. If the food product is a liquid, the liquid can be applied to the spot or zone 4 through use of a swab, spoon or a tubular straw or pipette. As previously noted, if the food product contains the allergenic substance, the reagent will change its appearance or color indicating the presence of the same.

It is contemplated that the doilies or mats may be sold in a stack of 100 or more, along with a tool or implement which can be used to apply the food product to the reagent spots.

The invention provides a simple and convenient manner of determining whether food products may contain an allergenic substance. The mats or doilies can be conveniently carried by the diner, or alternately, a food establishment may supply the mats to the diner.

As the food product is applied to the reagent, there is no possibility of the food being contaminated by the reagent as could occur if a dipstick was employed.

Various modes of carrying out the invention are contemplated as being within the scope of the following claims particularly pointing out and distinctly claiming the subject matter which is regarded as the invention.

I claim:

1. A method for the detection of allergenic substances in food products, comprising:

a) providing an absorbent dining mat used in a dining establishment, said dining mat having an upper surface, a peripheral edge, and a plurality of isolated zones disposed on said upper surface of said dining mat, each zone being spaced from adjacent zones and each zone containing a reagent which reacts with a specific allergenic substance in the food product to change the characteristics of said reagent, wherein a label is positioned adjacent each zone to identify the specific allergenic substance tested;

b) contacting at least one of said reagents located on said dining mat with a food product prepared in a dining establishment; and c) determining a change in the characteristics of said reagent as an indication of whether the food product prepared in said dining establishment contains the respective allergenic substance.

2. The method of claim 1, wherein the isolated zones are spaced inwardly of the peripheral edge of said mat.

* * * * *